United States Patent
Changoer et al.

(10) Patent No.: US 10,272,051 B2
(45) Date of Patent: Apr. 30, 2019

(54) METHOD TO TREAT ATOPIC DERMATITIS

(71) Applicant: AXIM Biotechnologies, Inc., New York, NY (US)

(72) Inventors: Lekhram Changoer, Ridderkerk (NL); George Anastassov, New York, NY (US)

(73) Assignee: Axim Biotechnologies, Inc., New York, NY (US)

( * ) Notice: Subject to any disclaimer, the term of this patent is extended or adjusted under 35 U.S.C. 154(b) by 0 days.

(21) Appl. No.: 16/106,524

(22) Filed: Aug. 21, 2018

(65) Prior Publication Data

US 2019/0060251 A1 Feb. 28, 2019

Related U.S. Application Data

(60) Provisional application No. 62/550,880, filed on Aug. 28, 2017.

(51) Int. Cl.
| | | |
|---|---|---|
| *A61K 9/00* | (2006.01) |
| *A61K 9/06* | (2006.01) |
| *A61K 9/68* | (2006.01) |
| *A61K 31/05* | (2006.01) |
| *A61K 47/44* | (2017.01) |
| *A61P 17/00* | (2006.01) |
| *A61P 17/02* | (2006.01) |
| *A61K 31/352* | (2006.01) |

(52) U.S. Cl.
CPC ............ *A61K 31/05* (2013.01); *A61K 9/0014* (2013.01); *A61K 9/0019* (2013.01); *A61K 9/0058* (2013.01); *A61K 9/06* (2013.01); *A61K 31/352* (2013.01); *A61K 47/44* (2013.01); *A61P 17/00* (2018.01); *A61P 17/02* (2018.01)

(58) Field of Classification Search
None
See application file for complete search history.

(56) References Cited

U.S. PATENT DOCUMENTS

2016/0235661 A1   8/2016   Changoer et al.

FOREIGN PATENT DOCUMENTS

| GB | 2542797 A | * | 4/2017 | ............. A61K 31/05 |
| WO | WO2009120080 A1 | | 10/2009 | |
| WO | WO2016209802 A1 | | 12/2016 | |
| WO | WO2017027553 A1 | | 2/2017 | |

OTHER PUBLICATIONS

Kim, J.S., et al. "Cannabinoid Receptors: Their Impact in Epidermal Differentiation and Possible Role in Treatment of Psoriasis", J. Am. Acad. Derm., AB 28, p. 1097, May 2015.

Campora, L., et al. "Cannabinoid Receptor Type 1 and 2 Expression in the Skin of Healthy Dogs and Dogs with Atopic Dermatitis", Am. J. Vet. Research, vol. 73, No. 7, p. 988-995, Jul. 2012.

* cited by examiner

*Primary Examiner* — Brian J Davis
(74) *Attorney, Agent, or Firm* — Premium IP Services, P.C.; Khanh T. Glatzel

(57) ABSTRACT

A method to treat the skin condition atopic dermatitis is described in this invention. The method comprises topical application of a composition containing cannabinoids, specifically cannabidiol and cannabigerol at a concentration of 3%-20% by weight of the composition. The method may further comprise administering chewing gum containing cannabinoids such as cannabidiol. Cannabidiol and cannabigerol may be sourced naturally or synthetically.

16 Claims, No Drawings

METHOD TO TREAT ATOPIC DERMATITIS

CROSS-REFERENCE TO RELATED APPLICATIONS

This application claims the benefit of U.S. Provisional Application No. 62/550,880, filed Aug. 28, 2017. Each of the above-referenced patent applications is incorporated by reference in its entirety.

BACKGROUND OF THE INVENTION

Field of the Invention

This invention concerns the field of treatment for skin conditions caused by alterations in the immune system. Various such skin conditions exist and various methods have been introduced for their treatment.

In particular, this invention concerns a method to treat atopic dermatitis using a topical composition for application on affected skin areas.

Description of the Related Technology

The *cannabis* plant has many naturally occurring substances that are of great interest in the fields of science and medicine. Isolated compounds from the *cannabis* plant include $\Delta^9$-tetrahydrocannabinol (THC), cannabidiol (CBD), cannabichromene (CBC), cannabigerol (CBG), cannabinol (CBN), cannabidivarin (CBDV), among many other compounds. While THC has psychoactive effects, CBD, CBC, CBG, and CBDV do not. Isolated alkaloid compounds from the *cannabis* plant are called cannabinoids. There are about one hundred and forty-one (141) cannabinoids that have been isolated from the *cannabis* plant. Many researchers have confirmed the medicinal value of cannabinoids. Cannabinoids have been investigated for possible treatment of seizures, nausea, vomiting, lack of appetite, pain, arthritis, inflammation, and other conditions.

Cannabinoids can be isolated by extraction or cold pressing from *cannabis* plants. Plants in the *cannabis* genus include *Cannabis sativa, Cannabis ruderalis*, and *Cannabis indica*. These plants are natural sources of cannabinoids. Cannabinoids are also available in synthetic forms. Methods to synthesize cannabinoids in lab setting were discovered and are still currently practiced. Synthetic cannabinoids are more targeted, in that the synthetic compound usually comes isolated without other cannabinoids and/or other compounds mixed in.

Nabilone (racemic(6aR,10aR)-1-hydroxy-6,6-dimethyl-3-(2-methyloctan-2-yl)-7,8,10,10a-tetrahydro-6H-benzo[c]chromen-9(6aH)-one), a synthetic cannabinoid, is believed to have fewer undesired side effects than THC. Nabilone mimics the chemical compound structure of THC. THC also exists in synthetic form under the name Dronabinol ((−)-(6aR,10aR)-6,6,9-trimythel-3-pentyl-6a,7,8,10a-tetrahydro-6H-benzo[c]chromen-1-ol)). The U.S. Food and Drug Administration approved nabilone and dronabinol for treatment of chemotherapy-induced nausea and vomiting and later for cachexia due to HIV/AIDS. In the United States, nabilone is marketed under the name Cesamet® and dronabinol under the name Marinol®. There are also generic versions of the drugs available on the market.

The IUPAC nomenclature of THC is (−)-(6aR,10aR)-6,6,9-trimethyl-3-pentyl-6a,7,8,10a-tetrahydro-6H-benzo[c]chromen-1-ol. CBD's IUPAC nomenclature is 2-((1S,6S)-3-methyl-6-(prop-1-en-2-yl)cyclo-hex-2-enyl)-5-pentylbenzene-1,3-diol). CBC has the IUPAC nomenclature of 2-methyl-2-(4-methylpent-3-enyl)-7pentyl-5-chromenol. CBG has the IUPAC nomenclature of 2-[(2E)-3,7-dimethylocta-2,6-dienyl]-5-pentyl-benzene-1,3-diol. These are among the most prominent compounds in the family of compounds extracted from the *cannabis* plant referred to as cannabinoids.

Cannabidiol is a major phytocannabinoid, accounting for up to 40% of the plant's extract. CBD is a CB-1 receptor antagonist, while THC is a CB-1 receptor agonist. A 2010 research found that *cannabis* strains with higher concentration of CBD did not produce the short-term memory impairment normally seen in high THC *cannabis* strain, a characteristic attributed to the CB-1 receptor antagonist nature of CBD. CBD is considered to have a wider scope of medical applications than THC.

Because it is a relatively unknown cannabinoid, cannabigerol (CBG) remains understudied and its effects are only just starting to become elucidated. CBG is a non-psychoactive cannabinoid found in the *cannabis* plant. All cannabinoids in the early stage of the *cannabis* plant's life begin as CBG. CBG is found in higher concentrations in hemp plants as opposed to marijuana plants, which are grown to have higher concentrations of tetrahydrocannabinol (THC). CBG has been found to act as a high affinity $\alpha_2$-adrenergic receptor agonist, a moderate affinity to $5\text{-}HT_{1A}$ receptor antagonist, and a low affinity $CB_1$ receptor antagonist. It binds with the $CB_2$ receptor, but it is currently unknown whether it acts as an agonist or antagonist.

Atopic dermatitis, also known as eczema, is a type of inflammation of the skin. It results in itchy, red, swollen, and cracked skin. Clear fluid may extravasate from the affected skin, which often thickens over time. The condition typically starts in childhood with fluctuating severity over the years.

The cause is unknown but believed to involve genetics, immune system dysfunction, environmental exposures, and altered permeability of the skin. About 30% of the people with atopic dermatitis have mutations in the gene for the production of filaggrin (FLG), which increase the risk for early onset of atopic dermatitis and developing asthma. Filaggrin plays an important role in keeping the skin surface slightly acidic; hence giving it anti-microbial effects. It breaks down into trans-urocanic acid, which keeps the pH low.

Evidence suggests that interleukin 4 (IL-4) is central in the pathogenesis of AD. Therefore, there is a rationale for targeting IL-4 with anti-IL-4 inhibitors. Other interleukins, such as IL-2 and IL-31 are also thought to play a role in atopic dermatitis. IL-2 therapy has been explored as a treatment for atopic dermatitis.

Abbreviations

AD: Atopic dermatitis
CB1: Cannabinoid receptors type 1
CB2: Cannabinoid receptors type 2
CBC: Cannabichromene
CBD: Cannabidiol
CBDV: Cannabidivarin
CBG: Cannabigerol
CBN: Cannabinol
eCB: Endocannabinoid
IL-4: Interleukin
THC: Tetrahydrocannabinol
THCV: Tetrahydrocannabivarin

SUMMARY

The present invention provides a method to treat atopic dermatitis using compositions containing cannabinoids, namely cannabidiol and cannabigerol. Cannabinoids are present at 3% to 20% by weight of the total composition. The composition may be gel, liquid, spray, powder, or ointment form. Cannabinoids may be sourced naturally or synthetically and may be nano-encapsulated or micro-encapsulated. This method to treat atopic dermatitis may further comprise oral administration of chewing gums containing cannabidiol concomitantly with the topical application. Application of topical composition may be twice daily for at least six (6) weeks, while chewing gum is consumed three times daily for at least six (6) weeks.

There is provided a method to treat atopic dermatitis, the method comprising administering a topical composition containing cannabinoids onto skin areas of a subject in need thereof.

There is provided a method to treat atopic dermatitis as above, wherein the cannabinoids are cannabidiol and cannabigerol at a total weight percent of 3% to 20% of the composition.

There is provided a method to treat atopic dermatitis as above, wherein the cannabigerol is present at a twice to three times the weight of cannabidiol.

There is provided a method to treat atopic dermatitis as above, wherein cannabinoids in the composition are sourced naturally or synthetic.

There is provided a method to treat atopic dermatitis as above, wherein cannabinoids in the composition are in powder form prior to incorporation into the composition.

There is provided a method to treat atopic dermatitis as above, wherein cannabinoids in the composition are micro-encapsulated.

There is provided a method to treat atopic dermatitis as above, wherein cannabinoids in the composition are nano-encapsulated with particle sizes of 20 to 40 nanometers.

There is provided a method to treat atopic dermatitis as above, wherein the composition further comprises hyaluronic acid derivative.

There is provided a method to treat atopic dermatitis as above, wherein the hyaluronic acid derivative is sodium oleyl hyaluronate.

There is provided a method to treat atopic dermatitis as above, wherein the composition further comprises at least one of omega-3 or omega-6 fatty acids.

There is provided a method to treat atopic dermatitis as above, wherein the composition further comprises plant extracts.

There is provided a method to treat atopic dermatitis as above, wherein the plant extracts are neem, *curcuma longa*, *rubia cardifolia*, or *wrightia tinctorial* extract.

There is provided a method to treat atopic dermatitis as above, wherein the composition further comprises cacao butter.

There is provided a method to treat atopic dermatitis as above, wherein the composition is in a hydro gel form, a liquid form, a spray form, a powder form, or an ointment form.

There is provided a method to treat atopic dermatitis as above, wherein the topical composition is applied twice a day for six weeks.

There is provided a method to treat atopic dermatitis as above, further comprising oral administration of chewing gums containing cannabinoids to the subject.

There is provided a method to treat atopic dermatitis as above, wherein the cannabinoid is cannabidiol and the chewing gums contains 10 milligrams of cannabidiol in each piece.

There is provided a method to treat atopic dermatitis as above, wherein the chewing gum contains 0.01% to 10% of cannabinoids by total weight of the chewing gum composition.

There is provided a method to treat atopic dermatitis as above, wherein the chewing gum is administered 3 times per day for six weeks.

DETAILED DESCRIPTION OF CERTAIN INVENTIVE EMBODIMENTS

This present invention is capable of being embodied in various forms. The description below of several embodiments is made with the understanding that the present disclosure is to be considered as an exemplification of the claimed subject matter and is not intended to limit the attached claims to the specific embodiments illustrated. The headings used throughout this disclosure are provided for convenience only and are not to be construed to limit the claims in any way. Embodiments illustrated under any heading may be combined with embodiments illustrated under any other heading.

As used herein, the verb "to comprise" in this description, claims, and other conjugations are used in its non-limiting sense to mean those items following the word are included, but items not specifically mentioned are not excluded.

Reference to an element by the indefinite article "a" or "an" does not exclude the possibility that more than one of the elements are present, unless the context clearly requires that there is one and only one of the elements. The indefinite article "a" or "an" thus usually means "at least one." Additionally, the words "a" and "an" when used in the present document in concert with the words "comprising" or "containing" denote "one or more." The word "cannabinoid" used in this description, claims, and other conjugations is used to mean any compound that interacts with a cannabinoid receptor and other cannabinoid mimetics, including, but not limited to, certain tetrahydropyran analogs (Δ9-tetrahydrocannabinol, Δ8-tetrahydrocannabinol, 6,6,9-trimythel-3-pentyl-6H-dibenzo[b,d]pyran-1-ol,3-(1,1-dimethylheptyl)-6,6a7,8,10,10a-hexahydro-1-1hydroxy-6,6-dimethyl-9H-dibezo[b,d]pyran-9-ol, (−)-(3S,4S)-7-hydroxy-delta-6-tetrahydrocannabinol-1,1-dimethylheptyl, (+)-(3S,4S)-7-hydroxy-Δ-6-tetrahydrocannabinol, and Δ8-tetrahydrocannabinol-11-oic acid); certain piperidine analogs (e.g., (−)-(6S,6aR,9R,10aR)-5,6,6a,7,8,9,10,10a-octahydro-6-methyl-1-3-[(R)-1-methyl-4-phenylbutoxy]-1,9-phenanthridinediol 1-acetate)); certain aminoalkylindole analogs (e.g., (R)-(+)-[2,3-dihydro-5-methyl-3-(4-morpholinylm-ethyl)-pyrrolo[1,2,3-de]-1,4-benzoxazin-6-yl]-1-naphthelenyl-methanone); certain open pyran-ring analogs (e.g., 2-[3-methyl-6-(1-methylethenyl-2-cyclohexen-1-yl]-5-pentyl-1,3-benzendi-ol, and 4-(1,1-dimethylheptyl)-2,3'-dihydroxy-6'-α-(3-hydroxypropyl)-1'-2',3',4',5',6'-hexahydrobiphenyl), their salts, solvates, metabolites, and metabolic precursors.

The word "cannabidiol" refers to cannabidiol and cannabidiol derivatives. As used in this application, cannabidiol is obtained from industrial hemp extract with a low amount of THC or from *cannabis* extract using high-CBD *cannabis* cultivars. Cannabidiol may also be synthetic.

The word "cannabigerol" refers to cannabigerol and cannabigerol derivatives. As used in this application, cannabigerol is derived from industrial hemp extract with a trace amount of THC or from *cannabis* extract. Cannabigerol may also be synthetic.

The phrase "atopic dermatitis" refers to the inflammation of the skin causing the skin to be red and itchy. It is also known as eczema.

The table below shows the primary cannabinoids in this invention, their abbreviations, and their chemical structures.

TABLE 1

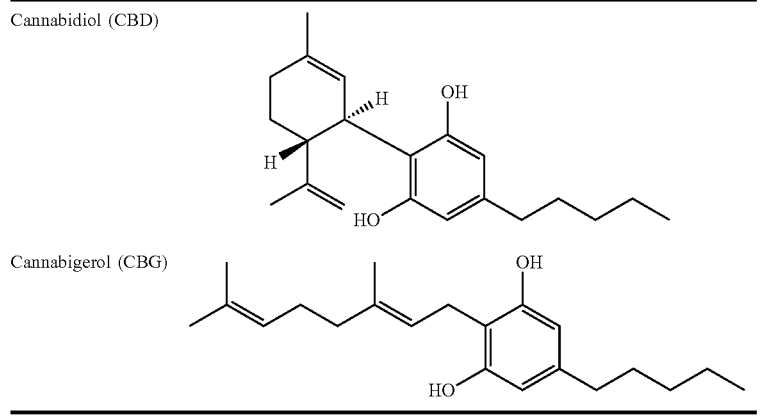

| Cannabidiol (CBD) | |
| Cannabigerol (CBG) | |

Embodiments of this application relate to methods to treat the skin condition atopic dermatitis caused by altered immune system response. The methods presented concerns using topical application compositions containing cannabinoids, in particular CBD and CBG, to be applied to the subject's skin area, and chewing gum containing CBD administered orally for trans-oral-mucosal delivery of cannabidiol (CBD).

In embodiments, the medicament used for this method of treatment may be a topical composition such as an oil, an ointment, a cream, or a powder containing cannabinoids, namely CBD and CBG, while other cannabinoids may be present. Cannabinoid oil may be from *cannabis* or hemp extraction and concentrated to reach desired cannabinoid concentrations. Cannabinoid acids may be decarboxylated during preparation to turn cannabinoid-acids into cannabinoids. After extraction from *cannabis* or hemp plant materials, cannabinoid extraction may be blended with other vegetable oils, such as hemp seed oil, sesame oil, coconut oil, among other suitable oils, to achieve desired concentration and/or viscosity. Blended vegetable oils containing cannabinoids may also be used to formulate other topical compositions.

Cannabinoid topical compositions for use in this invention may be prepared by preparing separate cannabinoid oils or solutions with different primary cannabinoids before the various cannabinoid oils or solutions may be combined to give the final cannabinoid topical composition. For example, CBD-rich oil may be prepared at a certain concentration and CBG-rich oil may be prepared at a certain concentration separately. The oil may then be blended together to achieve desired cannabinoid concentrations and used in topical application. The oils may also be incorporated into a cannabinoid topical composition with other ingredients. The oils may also be blended together before being incorporated into a topical composition.

CBG may be present at about twice to three times the amount of CBD by weight in this topical composition. Other weight ratios between CBG and CBD in this cannabinoid oil are contemplated.

In embodiments, cannabinoid compositions used in this method may contain CBD/CBG oil at 3%-20% by weight. The percentages given include both cannabinoids, for example the total weight percentage of CBD/CBG in the composition is 15%, as used in the experiment below. CBG may be present at twice to three times the amount of CBD in the same composition. Other ratios of CBG:CBD are contemplated. Other cannabinoids may be present at lower concentration, such as lower than 1% by weight. It is contemplated that CBD/CBG composition at 3-20% by weight percent of the total composition may be used in this treatment method according to embodiments. Preferably, CBD/CBG concentration in the topical composition use comprises more than 10% by weight of the composition.

Alternatively, cannabinoids may also be incorporated into the composition from crystalline and/or powder form. Cannabinoids used in these embodiments must be at a high purity, such as 99% purity, but could be lower or higher. Cannabinoids concentration in the composition used in this invention may be at 0.5-20% of the total composition by weight.

Crystalline cannabinoids may be isolated from *cannabis* extraction. *Cannabis* extraction is crystallized with C5-C12 alkane, then filtrated and vacuum dried to produce cannabinoid crystal at high purity. Crystalline cannabinoids may then be combined with vegetable oil such as hemp seed oil and used as medicament for topical application.

In embodiments, the medicament may also be a composition containing cannabinoids with additional components formulated into a composition for topical application. The cannabinoids in the formulation may be in nano-encapsulated form and the size of the particles is between 20 and 40 nm. The cannabinoids in these compositions may also be microencapsulated. Cannabinoids may be sourced naturally or synthetically.

In embodiments, the composition used in this method may further comprised hyaluronic acid (HA) derivatives. HA derivatives may include but is not limited to sodium oleyl hyaluronate, sodium hyaluronate, or sodium azidyl hyaluronate, among other HA derivatives. Other plant extract ingredients may be present in this composition, such as neem, *curcuma longa, rubia cardifolia, wrightia tinctorial* extracts, among other plant extracts. The composition may further comprise cacao butter, wherein cannabinoids are incorporated into cacao butter prior to being synthesized into the composition. Other components in this composition according to embodiments may include omega-3 and/or omega-6 fatty acids. Cannabinoids may be combined with omega-3 and/or omega-6 fatty acid.

The composition may further comprise other ingredients to effectuate the form in which the composition may be prior to usage. The composition may be prepared into a cream, an ointment, a gel, a hydro gel, a spray, a powder, or other composition form suitable for topical application. Preparation of the topical compositions containing cannabinoids according to embodiments may be by methods commonly known in the art.

In embodiments, additional medicaments used in this study were chewing gums containing CBD at 10 mg a piece. Chewing gums may be consumed by mastication, upon which CBD is released and absorbed through the oral mucosa in a controlled fashion.

Methods to make chewing gum containing cannabinoids may be found in U.S. Pat. Nos. 9,023,322 B2 and 9,433,601 B2. Cannabinoids are incorporated into the chewing gum by means of a carrier comprising internal voids. Suitable carriers include certain cellulose, such as microcrystalline cellulose derivatives, such as hemicellulose. The cellulose derivative may be of natural origin, e.g. dextran, agarose, agar, pectin, alginate, xanthan, chitosan, starch. Chewing gums made according to these patents may have a release profile increasing absorption of cannabinoids through the musical membrane.

In embodiments, different cannabinoids may be included in the chewing gum provided for treatment of atopic dermatitis. Other cannabinoids may be CBG, THC, THCV, CBDV, or other cannabinoids. Different concentrations of cannabinoid in chewing gums are contemplated. Cannabinoids may be present at 0.01 to 10% by total weight of the chewing gum.

Study Design

Three (3) subjects with present atopic dermatitis who had received no therapy for at least six (6) weeks prior to the study were selected. Two (2) subjects received treatment by topical application of CBD/CBG oil, and one (1) subject received treatment by topical application of CBD/CBG oil and oral mastication of chewing gums containing CBD. The study was conducted on lesions present on the subjects' arms. Control was by means of lesions of similar size and severity on the subjects' other arm.

Cannabinoid oil used in this study was CBD/CBG oil at 3% by weight (total weight percentage of CBD and CBG in the oil was 3%) and CBD/CBG oil at 15% by weight (total weight percentage of CBD and CBG in the oil was 15%). The percentages given included both cannabinoids, such that the total weight percentage of CBD/CBG in the oil was 3% or 15%. Other cannabinoids may be present at lower concentration, such as lower than 1% by weight.

Chewing gums containing CBD at 10 mg in each piece were provided for mastication three (3) times a day, concurrently with topical application of CBD/CBG oil. Each day the subject consumed three (3) pieces of chewing gum with 10 mg of CBD in each piece.

Each subject was evaluated for present skin lesions due to atopic dermatitis to choose lesions for this study. On the left arm of each subject, two skin lesions at least twenty (20) centimeters away from each other were selected for treatment. Two (2) corresponding skin lesions on the right arm were selected for control.

Each lesion was assessed with an adapted version of the severity scoring of Atopic Dermatitis Severity Index (SCORAD). The following symptoms were scored: erythema (redness), desquamation (scaling infiltration), induration (thickness), excoriations (scratch marks), lichenification (skin thickening). Each score was graded as follows: none=0, mild=1, moderate=2, severe=3.

The study was conducted by topical application of CBD/CBG oil to lesions present on the subject's skin. CBD/CBG oil may be applied as a thin layer on the subject's skin. In each subject, one lesion on the left arm received topical application of CBD/CBG oil at 15% by weight of the total composition, the other lesion of the left arm received topical application of CBD/CBG oil at 3% by weight of the total composition. In these oils, CBG is present at twice the amount of CBD by weight. Two lesions on the right arm were selected and received placebo (0% CBD/CBG oil) to serve as controls.

Two subjects receive topical application of CBD/CBG oil only. In a third subject, apart from the topical application of CBD/CBG oil as the previous two (2) subjects, chewing gums were given at 3 pieces per day (10 mg of CBD in each piece) and were consumed by mastication for a minimum of 30 minutes. Chewing gums were consumed concurrently with topical application of CBD/CBG oil to lesions present on the subject's skin.

Preparation of CBD/CBG Oil

*Cannabis sativa* L. plants are grown, harvested, and processed to produce a botanical extract with naturally occurring cannabinoids. This botanical extract is analyzed for cannabinoid content to ascertain the weight percentage of major cannabinoids, namely CBD and CBG. The botanical extract is then blended with hemp seed oil to give CBD/CBG oil ointment.

Two CBD/CBG oil types with different CBD/CBG concentrations were prepared. The first CBD/CBG oil had CBD and CBG, in combination, at 3% by weight of the total composition. The second CBD/CBG oil had CBD and CBG, in combination, at 15% by weight of the total composition. The ratio of CBG:CBD is 2:1 in each of these oil preparations.

A third oil comprised only hemp seed oil and contained no CBD, CBG, or other cannabinoids. This third oil served as placebo in this experiment.

CBG/CBD oil was supplied by Axim Biotechnologies, Inc. The CBG/CBD strains were obtained from the company Ecohemp SRL.

Drug Treatment Procedure and Administration

Subjects received treatment twice daily for six (6) weeks as follows:

Each of the first two (2) subjects received topical application of a thin layer of 3% CBG/CBD oil on the upper lesion and 15% CBG/CBD oil on the lower lesion of the left arm and placebo (0% CBG/CBD oil) on the two lesions of the right arm. The treatment was given twice daily.

A third subject received topical application of a thin layer of 3% CBG/CBD oil on the upper lesion and 15% CBG/CBD oil on the lower lesion of the left arm and placebo (0% CBG/CBD oil) on the two lesions of the right arm twice daily and 3 pieces of chewing gum containing CBD at 10 mg in each piece, which were consumed daily by mastication.

Scoring of the lesions was by an adapted version of Atopic Dermatitis Severity Index (SCORAD), which is Table 1 as follows:

TABLE 2

| Symptom | Grading |
|---|---|
| Erythemda (redness) | |
| Desquamation (scaling) | |
| Infiltration, induration (thickness) | |
| Excoriations (scratch marks) | |
| Lichenification (skin thickening) | |

Grading was given by score from 0-3. Each score was graded as follows: none=0, mild=1, moderate=2, severe=3.

At the endpoint of the study, results were the difference as percentage of improvement between the left and right corresponding lesions. Lesions on the right arms are control samples. The following was the result of the study as described herein.

TABLE 3

| Condition | Subject | % Improvement of 3% CBD/CBG oil | % Improvement of 15% CBD/CBG oil | % Improvement of 15% CBD/CBG oil + CBD chewing gum |
|---|---|---|---|---|
| Atopic dermatitis | Subject 1 | 0 | 22 | n/a |
| Atopic dermatitis | Subject 2 | 0 | 11 | n/a |
| Atopic dermatitis | Subject 3 | 0 | n/a | 33 |

Discussion

Treatment by 3% CBG/CBD oil treatment showed no improvement on the lesions. The 15% CBG/CBD oil treatment showed 11% and 22% improvement on the two (2) subjects treated without CBD chewing gum. The 15% CBG/CBD oil treatment on the third subject also treated with 3 pieces of CBD chewing gum daily showed a 33% improvement. The improvement was intra-specimen, where the subjects' other lesions served as their own controls.

Due the systemic penetration of the active ingredients (CBG/CBD), an overall improvement may have occurred for both the studied lesions. This may have negatively influenced the perceived effectiveness of the treatment, since CBD/CBG at a lower dose may not have penetrated the skin very well. CBG was dosed twice as much as CBD, and as such might counteract some unintended actions of CBD, just like CBD is thought to counteract the cognitive impairment caused by tetrahydrocannabinol (THC).

Activation of peripheral CB1 receptors contributes to hemorrhagic and endotoxin-induced hypotension. Both CBG and CBD act as CB1 antagonists, which might suggest a possible mechanism that explains a reduction in redness in skin lesions through reduction of vasodilatation. This is supported by the finding that cannabinoids can inhibit inflammatory cytokines and angiogenic growth factors such as hypoxia inducible factor-1 $\alpha$(HIF-1 $\alpha$), vascular endothelial growth factor (VEGF), matrix metalo-proteinases (MMPs), basic fibroblast growth factor (bFGF), Angiopoietin-2, interleukin-8 (IL-8), IL-17, and IL-2 as well as cellular adhesion molecule 1 (ICAM-1) and vascular cell adhesion molecule-1 (VCAM-1) both in vivo and in vitro. Contrary to these findings it seems that CBD induced CB1 activation causes endothelium-dependent vasorelaxation of human mesenteric arteries.

The results from this study indicate a possible Th1/Th2 rebalancing mechanism. Despite the fact that only two concentrations have been used, there seems to be a clear dose-response effect, whereby higher doses (15% CBD/CBG oil) are effective where lower doses (3% CBD/CBG oil) do not show any effect. Factors influencing the dose effect might be a limited sufficient skin penetration, since skin penetration of cannabinoids may be poor.

The results present evidence for a possible synergistic role of CBD and CBG in dermatological conditions such as atopic dermatitis. Restoring the Th1/Th2 balance is thought to be the key mechanism of action, with a possible additional direct inhibiting effect of CBG on hyper proliferation of skin cells (scaling).

CONCLUSION

Topical application of cannabinoid oil containing CBD and CBG shows efficacy in treating atopic dermatitis. Improvement in symptoms as graded by the Atopic Dermatitis Severity Index shows efficacy in treating skin lesions using this topical application. Where chewing gum with CBD is consumed concurrently with topical application of CBD/CBG oil, increased efficacy is noted.

REFERENCES

Ando T, Xiao W, Gao P, Namiranian S, Matsumoto K, Tomimori Y, et al. *Critical Role for Mast Cell Stat5 Activity in Skin Inflammation*. Cell Reports. 6(2):366-76.

Biedermann T, Skabytska Y, Kaesler S, Volz T. *Regulation of T Cell Immunity in Atopic Dermatitis by Microbes: The Yin and Yang of Cutaneous Inflammation*. Frontiers in Immunology. 2015; 6(353).

Biro T, Toth B I, Hasko G, Paus R, Pacher P. *The Endocannabinoid System of The Skin in Health and Disease: Novel Perspectives and Therapeutic Opportunities*. Trends in Pharmacological Sciences. 2009; 30(8):411-20.

Borrelli F, Fasolino I, Romano B, Capasso R, Maiello F, Coppola D, et al. *Beneficial Effect of the Non-Psychotropic Plant Cannabinoid Cannabigerol on Experimental Inflammatory Bowel Disease*. Biochemical Pharmacology. 2013; 85(9):1306-16.

Borrelli F, Pagano E, Romano B, Panzera S, Maiello F, Coppola D, et al. *Colon Carcinogenesis is Inhibited by The TRPM8 Antagonist Cannabigerol, a Cannabis-Derived Non-Psychotropic Cannabinoid*. Carcinogenesis. 2014; 35(12):2787-97.

Brenneisen R, Egli A, Elsohly M A, Henn V, Spiess Y. *The Effect of Orally and Rectally Administered Delta 9-Tetrahydrocannabinol on Spasticity: a Pilot Study With 2 Patients*. International Journal of Clinical Pharmacology and Therapeutics. 1996; 34(10):446-52.

Campos A C, Moreira F, Gomes F V, Del Bel E A, Guimarães F S. *Multiple Mechanisms Involved in the*

*Large-Spectrum Therapeutic Potential of Cannabidiol in Psychiatric Disorders.* Philosophical Transactions of the Royal Society of London Series B, Biological Sciences. 2012; 367(1607):3364-78.

Cascio M, Gauson L, Stevenson L, Ross R, Pertwee R. *Evidence that the Plant Cannabinoid Cannabigerol is a Highly Potent A(2)-Adrenoceptor Agonist and Moderately Potent 5HT(1A) Receptor Antagonist.* Br. J. Pharmacol. 2010; 159(1):129-41.

Cheng Y, Hitchcock S A. *Targeting Cannabinoid Agonists for Inflammatory and Neuropathic Pain.* Expert Opinion on Investigational Drugs. 2007; 16(7):951-65.

Cuba L F, Salum F G, Cherubini K, Figueiredo M A. *Cannabidiol: An Alternative Therapeutic Agent for Oral Mucositis?* Journal of Clinical Pharmacy and Therapeutics. 2017.

Guttman-Yassky E, Krueger J G, Lebwohl M G. *Systemic Immune Mechanisms in Atopic Dermatitis and Psoriasis with Implications for Treatment.* Experimental Dermatology. 2017.

Iseger T A, Bossong M G. *A Systematic Review of The Antipsychotic Properties of Cannabidiol in Humans.* Schizophrenia Research. 2015; 162(1-3):153-61.

Jäger A, Dardalhon V, Sobel R A, Bettelli E, Kuchroo V K. *Th1, Th17 and Th9 Effector Cells Induce Experimental Autoimmune Encephalomyelitis with Different Pathological Phenotypes.* Journal of Immunology (Baltimore, Md.: 1950). 2009; 183(11):7169-77.

Kinghorn A D, Falk H, Gibbons S, Kobayashi J. Phytocannabinoids: *Unraveling the Complex Chemistry and Pharmacology of Cannabis sativa*: Springer International Publishing; 2017.

Lambert D M, Fowler C J. *The Endocannabinoid System: Drug Targets, Lead Compounds, and Potential Therapeutic Applications.* Journal of Medicinal Chemistry. 2005; 48(16):5059-87.

Maccarrone M, Bab I, Biro T, Cabral G A, Dey S K, Di Marzo V, et al. *Endocannabinoid Signaling at the Periphery: 50 Years After THC.* Trends in Pharmacological Sciences. 2015; 36(5):277-96.s Mashiko S, Bouguermouh S, Rubio M, Baba N, Bissonnette R, Sarfati M. *Human Mast Cells Are Major Il-22 Producers in Patients with Psoriasis and Atopic Dermatitis.* The Journal of Allergy and Clinical Immunology. 2015; 136(2):351-9.e1.

McGilveray I J. *Pharmacokinetics of Cannabinoids.* Pain Research & Management. 2005; 10 Suppl A:15a-22a.

Mechoulam R, Peters M, Murillo-Rodriguez E, Hanuš L O. *Cannabidiol—Recent Advances.* Chemistry & Biodiversity. 2007; 4(8):1678-92.

Nam G, Jeong S K, Park B M, Lee S H, Kim H J, Hong S P, et al. *Selective Cannabinoid Receptor-1 Agonists Regulate Mast Cell Activation in an Oxazolone-Induced Atopic Dermatitis Model.* Annals of dermatology. 2016; 28(1): 22-9.

Raphael I, Nalawade S, Eagar T N, Forsthuber T G. *T Cell Subsets and Their Signature Cytokines in Autoimmune and Inflammatory Diseases.* Cytokine. 2015; 74(1):5-17.

Russo E B, Burnett A, Hall B, Parker K K. *Agonistic Properties of Cannabidiol at 5-HT1a Receptors.* Neurochemical Research. 2005; 30(8): 1037-43.

Ryberg E, Larsson N, Sjögren S, Hjorth S, Hermansson N, Leonova J, et al. *The Orphan Receptor GPR55 is a Novel Cannabinoid Receptor.* Br. J. Pharmacol. 2007; 152(7): 1092-101.

Small-Howard A L, Shimoda L M, Adra C N, Turner H. *Anti-Inflammatory Potential of CB1-Mediated Camp Elevation in Mast Cells.* The Biochemical Journal. 2005; 388(Pt 2):465-73.

Sugawara K, Biro T, Tsuruta D, Toth B I, Kromminga A, Zakany N, et al. *Endocannabinoids Limit Excessive Mast Cell Maturation and Activation in Human Skin.* The Journal of Allergy and Clinical Immunology. 2012; 129 (3):726-38.e8.

Toh M R, Teo V, Kwan Y H, Raaj S, Tan S Y, Tan J Z. *Association Between Number of Doses Per Day, Number of Medications and Patient's Non-Compliance, and Frequency of Readmissions in a Multi-Ethnic Asian Population.* Preventive Medicine Reports. 2014; 1:43-7.

Turcotte C, Blanchet M R, Laviolette M, Flamand N. *The CB2 Receptor and Its Role as a Regulator of Inflammation.* Cellular and Molecular Life Sciences: CMLS. 2016; 73(23):4449-70.

Valdeolivas S, Navarrete C, Cantarero I, Bellido M L, Munoz E, Sagredo O. *Neuroprotective Properties of Cannabigerol In Huntington's Disease: Studies in R6/2 Mice and 3-Nitropropionate-Lesioned Mice.* Neurotherapeutics: The Journal of the American Society for Experimental NeuroTherapeutics. 2015; 12(1): 185-99.

Varga K, Wagner J A, Bridgen D T, Kunos G. *Platelet- and Macrophage-Derived Endogenous Cannabinoids are Involved in Endotoxin-Induced Hypotension.* FASEB Journal: Official Publication of the Federation of American Societies for Experimental Biology. 1998; 12(11): 1035-44.

WebMD. *Atopic Dermatitis (Eczema)—Topic Overview*: WebMD; 2017 [Available at: http://www.webmd.com/skin-problems-and-treatments/eczema/tc/atopic-dermatitis-topic-overview#1.

Weijenberg R A, Lobbezoo F, Knol D L, Tomassen J, Scherder E J. *Increased Masticatory Activity and Quality of Life in Elderly Persons with Dementia—a Longitudinal Matched Cluster Randomized Single-Blind Multicenter Intervention Study.* BMC Neurology. 2013; 13:26.

Weijenberg R A, Lobbezoo F. *Chew the Pain Away: Oral Habits to Cope with Pain and Stress and to Stimulate Cognition.* BioMed Research International. 2015; 2015: 149431.

Weiss L, Zeira M, Reich S, Har-Noy M, Mechoulam R, Slavin S, et al. *Cannabidiol Lowers Incidence of Diabetes in Non-Obese Diabetic Mice.* Autoimmunity. 2006; 39(2): 143-51.

Wikipedia. *Atopic dermatitis: Wikipedia;* 2017 [Available at: https://en.wikipedia.org/wiki/Atopic_dermatitis#Treatments.

All references, including publications, patent applications, and patents cited herein are hereby incorporated by reference to the same extent as if each reference were individually and specifically indicated to be incorporated by reference and were set forth in its entirety herein.

It will be readily apparent to those skilled in the art that a number of modifications and changes may be made without departing from the spirit and the scope of the present invention. It is to be understood that any ranges, ratios, and range of ratios that can be derived from any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art will appreciate that such values are unambiguously derivative from the data presented herein.

What is claimed is:

1. A method to treat atopic dermatitis, comprising:
administering a topical composition containing cannabinoids onto skin areas of a subject in need thereof,
wherein the cannabinoids are cannabidiol and cannabigerol at a total weight percent of 3% to 20% of the composition.

2. The method of claim 1, wherein the cannabigerol is present at a twice to three times the weight of cannabidiol.

3. The method of claim 1, wherein the cannabinoids in the composition are in powder form prior to incorporation into the composition.

4. The method of claim 1, wherein the cannabinoids in the composition are in crystalline form prior to incorporation into the composition.

5. The method of claim 1, wherein the cannabinoids in the composition are microencapsulated.

6. The method of claim 1, wherein the cannabinoids in the composition are nanoencapsulated with particle sizes of 20 to 40 nanometers.

7. The method of claim 1, wherein the composition further comprises a hyaluronic acid derivative.

8. The method of claim 7, wherein the hyaluronic acid derivative is sodium oleyl hyaluronate.

9. The method of claim 8, wherein the composition further comprises at least one of omega-3 or omega-6 fatty acids.

10. The method of claim 9, wherein the composition further comprises cacao butter.

11. The method of claim 1, wherein the composition is in a hydro gel form, a liquid form, a spray form, or a powder form.

12. The method of claim 1, wherein the topical composition is applied twice a day for six weeks.

13. The method of claim 1, further comprising oral administration of chewing gums containing at least one cannabinoid to the subject.

14. The method of claim 13, wherein the at least one cannabinoid in the chewing gums is cannabidiol and the chewing gums contains 10 milligrams of cannabidiol in each piece.

15. The method of claim 13, wherein the chewing gums contain 0.01% to 10% of cannabinoids by total weight of the chewing gum composition.

16. The method of claim 13, wherein the chewing gums are administered 3 times per day for six weeks.

* * * * *